United States Patent [19]

Merkel

[11] Patent Number: 4,558,036

[45] Date of Patent: Dec. 10, 1985

[54] ACTAPLANIN ANTIBIOTICS

[75] Inventor: Kurt E. Merkel, Mooresville, Ind.

[73] Assignee: Eli Lilly and Company, Indianapolis, Ind.

[21] Appl. No.: 581,016

[22] Filed: Feb. 17, 1984

[51] Int. Cl.[4] .................. A61K 37/00; C07C 103/52; C07H 17/08

[52] U.S. Cl. ......................... 514/9; 536/4.1; 536/16.8; 536/18.1; 260/112.5 R

[58] Field of Search ...... 536/4.1, 16.8, 18.1; 424/118, 181, 180; 514/9; 260/112.5 R

[56] References Cited

U.S. PATENT DOCUMENTS

| | | | |
|---|---|---|---|
| 3,928,571 | 12/1975 | Raun | 424/118 |
| 3,952,095 | 4/1976 | Hamill et al. | 424/118 |
| 4,064,233 | 12/1977 | Hamill et al. | 424/118 |
| 4,115,552 | 9/1978 | Hamill et al. | 424/118 |
| 4,322,343 | 3/1982 | Debono | 260/8 |
| 4,322,406 | 12/1980 | Debono et al. | 424/118 |
| 4,375,513 | 3/1983 | Debono et al. | 435/169 |
| 4,479,897 | 10/1984 | Hunt | 260/112.5 R |

OTHER PUBLICATIONS

Kalman et al., *J. Amer. Chem. Soc.*, 102, No. 3 (1980) 897–905.

*Primary Examiner*—Johnnie R. Brown
*Assistant Examiner*—Elli Peselev
*Attorney, Agent, or Firm*—William B. Scanlon; Arthur R. Whale

[57] ABSTRACT

Antibiotic A4696 factor H is isolated from the purified antibiotic complex produced by *Actinoplanes missouriensis* ATCC 31683 and exhibits excellent activity vs. gram-positive bacteria.

12 Claims, No Drawings

ACTAPLANIN ANTIBIOTICS

BACKGROUND OF THE INVENTION

This invention relates to glycopeptide antibiotics. In particular, it relates to an antibiotic compound which belongs to the actaplanin antibiotics and which is designated herein as actaplanin H.

The actaplanin antibiotics are structurally complex cyclic glycopeptides which are therapeutically useful as growth promotants and feed efficiency improvers in important animals.

Actaplanin (A4696) is described by Hamill et al., U.S. Pat. No. 3,952,095, and factors A and "B" thereof are described in U.S. Pat. No. 4,115,552. Previously unisolated and unrecognized A4696 factors are described by Debono et al., in U.S. Pat. No. 4,322,406. Debono, U.S. Pat. No. 4,322,343, also describes the pseudoaglycone obtained by the complete hydrolysis of actaplanin. Hunt and Merkel in copending application Ser. No. 488,967 filed April 27, 1983, U.S. Pat. No. 4,479,897, issued Oct. 30, 1984, describe actaplanin factors which are obtained by the partial acidic hydrolysis of the known actaplanins.

The actaplanin antibiotics possess activity against gram-positive microorganisms including pathogenic strains of staphylococcus and streptococcus.

SUMMARY

Actaplanin factor H, also designated as antibiotic A4696H, is produced by culturing *Actinoplanes missouriensis* ATCC 31683 under submerged aerobic fermentation conditions. The actaplanin complex comprising factor H and the coproduced known factors A, $B_1$, $B_2$, $B_3$ and $C_{1a}$ is separated from the filtered fermentation medium and purified. Factor H and the other factors are then separated from the purified complex by high performance liquid chromatography.

DETAILED DESCRIPTION

Antibiotic A4696 factor H provided by this invention is represented by the following structural formula 1

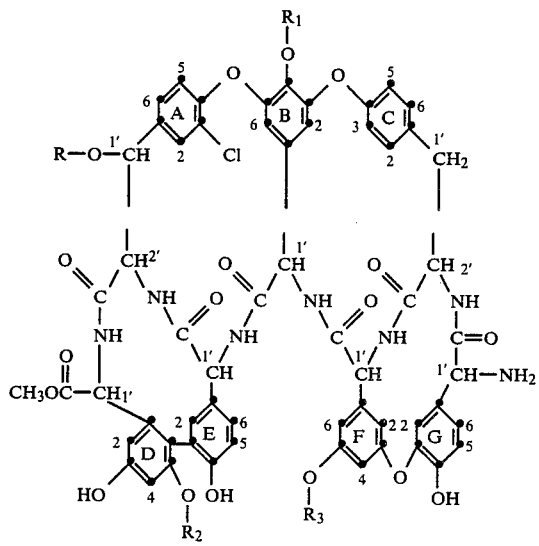

wherein R is L-ristosamine; $R_1$ is glucose; $R_2$ and $R_3$ are both mannose.

Factor H is produced by culturing *Actinoplanes missouriensis* strain ATCC 31683 under submerged aerobic fermentation conditions until a substantial amount of antibiotic activity is produced in the culture medium. *A. missouriensis* ATCC 31683 also produced A4696 factors A, $B_1$, and $B_2$ as the most abundant factors while factors $B_3$, and $C_{1a}$ are coproduced minor factors. As with many fermentations which produce multifactors, the amount of each factor produced may vary from fermentation to fermentation. Factor H is generally present in amounts of between about 2% and about 15% of the total antibiotic activity produced.

The factor H producing microorganism, the fermentation conditions for culturing the strain, the coproduced factors $B_3$ and $C_{1a}$ and the isolation of the factor complex are described in U.S. Pat. No. 4,322,406 The *A. missouriensis* ATCC 31683 which produces factor H is claimed in U.S. Pat. No. 4,375,513.

Factor H was a previously unrecognized coproduced factor of *A. missouriensis* strain ATCC 31683 which occurred in the isolated antibiotic complex. Of the known A4696 factors, factor H is closest in structure to factor $B_2$. Factor H differs structurally from $B_2$ in that it lacks the methyl group attached to ring F (Formula 1) adjacent to the -O-mannosyl group in factor $B_2$. Factor H can be designated as demethyl factor $B_2$.

The molecular weight of factor H differs by 14 from the molecular weight of factor $B_2$ as determined by Fast Atom Bombardment mass spectroscopy.

| Factor | MW-FAB/MS |
|---|---|
| H | 1792 |
| $B_2$ | 1806 |

Factor H can be separated from the coproduced factors via HPLC. The following retention times for the factors A, $B_1$, $B_2$ and H were obtained in the chromatogram described below. A liquid chromatograph (Waters Associates, Milford, Mass.) equipped with a Model 660 solvent programmer, two Model 6000 solvent delivery systems, a Radial Compression System (RCM-100), a Radial Pak $C_{18}$ cartridge, 8 mm×100 mm, 5μ and a Model 440 absorbance detector set at 254 nm was used. The mobile phase consisted of Solvent A: 50 ml acetonitrile and 950 ml aqueous solution containing 0.2% triethylamine adjusted with $H_3PO_4$ to pH 3. Solvent B: 400 ml acetonitrile and 600 ml of the same aqueous solution used in Solvent A. The solvent programmer settings were 0–60% B, curve 7, 20 minutes. The flow rate was 4 ml/min. The sample load was ca. 50 μg. and the detector setting was 0.05 AUFS. In this chromatograph the retention times for the indicated factors were as follows:

| Factor | Retention Time (min) |
|---|---|
| H | 10.53 |
| A | 6.17 |
| $B_1$ | 7.47 |
| $B_2$ | 11.61 |

The $^1$H NMR assignments for factor H at 333° K. in DMSO (360 MHz) are listed below. The numerals and letters refer to the arbitrary numbering system shown in formula 1. The protons of the mannose and glucose sugars other than those indicated are not assigned.

| Assignment | δ |
| --- | --- |
| A-NH | 6.94 |
| A-2' | 4.22 |
| A-1' | 5.09 |
| A-2 | 7.73 |
| A-5 | 7.29 |
| A-6 | 7.36 |
| B-NH | 7.97 |
| B-1' | 5.68 |
| B-2 | 5.76 |
| B-6 | 5.14 |
| C-NH | 7.37 |
| C-2' | 4.93 |
| C-1' | 3.27 & 2.83 |
| C-2 | 7.59 |
| C-3 | 7.08 |
| C-5 | 7.21 |
| C-6 | 7.10 |
| D-NH | 8.74 |
| D-1' | 4.55 |
| (—OCH$_3$) | 3.71 |
| D-2 | 6.28 |
| D-4 | 6.80 |
| E-NH | 8.50 |
| E-1' | 4.50 |
| E-2 | 7.12 |
| E-5 | 6.76 |
| E-6 | 6.76 |
| F-NH | 7.64 |
| F-1' | 5.35 |
| F-2 | 6.59 |
| F-4 | not assigned |
| F-6 | 6.62 |
| G-1' | 4.47 |
| G-2 | 6.56 |
| G-5 | 6.89 |
| G-6 | 7.08 |
| *Glu Anomeric | 5.43 |
| *Man I (R$_3$) Anomeric | 5.33 |
| *Man II (R$_2$) Anomeric | 5.26 |
| *Rist Anomeric | 4.72 |

*Note Other sugar resonances not assigned.

Factor H exhibits excellent activity against gram-positive microorganisms while it is substantially less active against the gram-negative microorganisms. The activity of factor H against several strains of staphylococcus and streptococcus is shown in Table 1. The activity is expressed in minimum inhibitory concentrations (MIC) determined by the agar dilution method.

TABLE 1

| Antibacterial Activity of Factor H vs. Gram-Positive Bacteria | |
| --- | --- |
| Test Bacteria[1] | Mic (μg/ml) |
| *Staphylococcus aureus* X1.1 | 2 |
| *Staphylococcus aureus* V41 | 4 |
| *Staphylococcus aureus* X400 | 8 |
| *Staphylococcus aureus* S13E | 4 |
| *Staphylococcus epidermidis* EPI1 | 16 |
| *Staphylococcus epidermidis* 222 | 2 |
| *Streptococcus pyogenes* C203 | .5 |
| *Streptococcus pneumoniae* Park | .5 |
| Streptococcus group D X66 | 1 |
| Streptococcus group D 2041 | 2 |

[1]The numeral-letter designates strains

The observed MIC. for factor H against test strains of *H. influenzae, E. coli,* Klebsiella, Enterobacter, Salmonella, Pseudomonas, Serratia, Shigella, and Proteus were above 128 μg/ml.

Factor H can form acid addition salts with suitable acids. Such acids include hydrochloric acid, hydrobromic acid, sulfuric acid, phosphoric acid, and like acids. Salts may also be formed with sulfonic acids, for example, methanesulfonic acid, benzenesulfonic acid, toluenesulfonic acid, and the like. The salts of factor H can be used as pharmaceutically acceptable forms of the antibiotic or they may be employed in the isolation and purification thereof. Preferred pharmaceutically acceptable salts are the hydrochloride, sulfate and phosphate salts. The acid addition salts of factor H are prepared in a conventional manner, e.g. by neutralization of the basic amino group.

Factor H and the pharmaceutically acceptable salts thereof are useful in the treatment and control of infections in man and animals caused by gram-positive bacteria, in particular, the staphylococcus and the streptococcus. The antibiotic or a salt thereof may be administered parenterally or orally for the treatment of systemic infections or topically for external infections. For parenteral use the antibiotic or a pharmaceutically acceptable non-toxic salt thereof is formulated with a suitable physiologically acceptable diluent. Such diluents as Water-for-Injection, 0.9% saline, dextrose or glucose may be used. For oral administration the antibiotic or salt may be administered in capsules or suspensions. For topical use the antibiotic or preferably a suitable salt form thereof may be made up in solution at a concentration of between about 0.5% and 25%. Such solution may also desirably contain a surface active agent, solubilizer, etc.

Accordingly, in one of its aspects this invention provides a method for treating infections in a mammal which comprises administering an antibiotically effective amount of actaplanin factor H or a pharmaceutically acceptable non-toxic salt thereof. The antibiotic factor or a salt thereof may be administered in a dose of between about 100 mg to about 2 g. The particular dosage and the frequency of administration may vary depending on such factors as the type and severity of the infection, the situs of the infection, the age and general health of the patient, and the extent to which the particular host may tolerate the antibiotic.

Antibiotic A4696 factor H like the other structurally related A4696 factors may be used as a growth promotant and feed efficiency enhancer in poultry, swine, sheep and cattle. For such use the antibiotic or an acceptable salt thereof is incorporated in the feedstuff of the animal or in its drinking water. For increasing the feed efficiency of ruminant animals the antibiotic is preferably incorporated in the animal's feed at approximately a level of between about 2 g and about 200 g per ton of feed. To promote the growth of swine the antibiotic is incorporated in the feed at a concentration sufficient to administer to the animal between about 0.5 mg/kg to about 25 mg/kg of body weight.

The method provided by this invention for enhancing feed efficiency in ruminant animals comprises administering a propionate increasing amount of factor H to a ruminant, eg. a cow or a sheep. Preferably, factor H is incorporated in the feed of such animals in an amount between about 2 g and about 200 g per ton of feed. This rate should supply to the animal an adequate effective dose of at least between about 1 mg/kg/day and about 100 mg/kg/day.

Ruminant animals having a developed rumen, i.e. weaned animals on solid food, metabolize carbohydrates via the formation of volatile fatty acids (VFA). Acids such as acetic acid, propionic acid and butyric acids or esters thereof comprise the VFA in the rumen. The VFA's are utilized as food by the animal after absorption from the gut. The utilization of butyrates and acetates is inefficient since a portion of each in also coverted to methane gas which is lost from the gut. Propionates on the other hand are not converted to methane and are thus more efficient energy sources for the animal. Accordingly, it is known that the efficiency of carbohydrate utilization can be increased by treatments which result in the animal's production of propionate rather than acetates and butyrates. Actaplanin factor H, when administered by the method of this invention, increases food efficiency by increasing propionates relative to acetates and butyrates in the animal's rumen.

As described hereinabove, actaplanin factor H is also useful for promoting the growth of poultry and swine. According to a further aspect of this invention, there is provided a method for promoting the growth of poultry and swine which comprises orally administering to said animals an effective growth promoting amount of factor H or a pharmaceutically acceptable salt thereof. Preferably, the antibiotic is incorporated in the animal's feed and in the case of chickens and turkeys it may be added to the fowl's drinking water.

In the practice of the veterinary methods of this invention economical forms of actaplanon factor H are desirably used. Salt forms such as the hydrochloride and sulfate salts are preferred. Likewise, in the ruminant feed utilization method the actaplanin factor need not be used in pure form. Preferably, the dried whole fermentation broth containing factor H along with the dried mycelium is used as an economical form of factor H. Also, factor H containing small amounts of other A4696 factors coproduced in the fermentation may be used in such methods without any untoward effect.

The following Example describes the separation and purification of factor H from the purified antibiotic complex isolated from the fermentation of *Actinoplanes missouriensis* ATCC 31683. The fermentation and the isolation and purification of the complex are described in detail by U.S. Pat. No. 4,322,406 and, in particular, Example IB through E.

EXAMPLE 1

Separation of A4696H from A4696 complex

One gram of the purified A4696 complex was dissolved in 10 ml of water and the solution was filtered through a 0.22 μm membrane filter (catalog No. GSWP01300, Millipore Corporation, Bedford, MA, 01730). The filtrate was divided into 2 ml portions and each portion was chromatographed over a 37 mm×350 mm column containing C-18 reversed phase adsorbent (ca. 10-20 μm). The column was eluted with an aqueous acetonitrile gradient containing 7.5%-10% of acetonitrile. The aqueous phase of the gradient contained triethylamine and the pH was adjusted to 3 with 10% aqueous phosphoric acid prior to the addition of acetonitrile.

The column effluent was monitored with a UV-detector set at 254 nm and fractions were combined accordingly. The A4696 factor H containing fractions from twelve such chromatographic separations were combined and concentrated under high vacuum to one-tenth the original volume. The pH of the concentrate was adjusted to pH 7 with 0.1N aqueous sodium hydroxide and the concentrate loaded on a 8 mm×250 mm column containing freshly conditioned Diaion HP20 resin (Mitsubishi Chemical Industries, Ltd., Tokyo 100, Japan). The column was washed repeatedly with water and factor H was then eluted with aqueous methyl alcohol containing 30% to 50% methyl alcohol. The eluent was concentrated under high vacuum to remove methyl alcohol and the concentrate was evaporated to dryness. Pure A4696 factor H was obtained, 0.0480 g, as a white amorphous solid.

I claim:

1. A compound of the formula

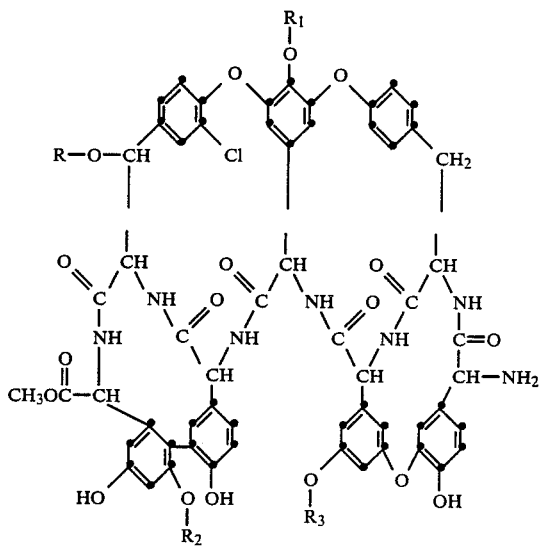

wherein R is L-ristosamine; $R_1$ is glucosyl; $R_2$ and $R_3$ are both mannose; and the pharmaceutically acceptable non-toxic salts thereof.

2. The compound of claim 1 as the free base.

3. The compound of claim 1 as a pharmaceutically acceptable non-toxic salt.

4. The compound of claim 2 in pure form.

5. A method for treating infections in a mammal which comprises administering an antibiotically effective amount of actaplanin factor H of claim 1 or a pharmaceutically acceptable non-toxic salt thereof.

6. A method for increasing the efficiency of feed utilization by a ruminant animal having a developed rumen function which comprises orally administering to said ruminant a propionate-increasing amount of actaplanin factor H of claim 1 or a pharmaceutically acceptable salt thereof.

7. The method of claim 6 wherein actaplanin factor H is administered at a rate of between about 1 mg/kg/day to about 100 mg/kg/day.

8. The method of claim 7 wherein the ruminant animal is a cow.

9. The method of claim 7 wherein the ruminant animal is a sheep.

10. A method for promoting growth in poultry and swine which comprises orally administering to said animal an effective growth promoting amount of actaplanin factor H of claim 1 or a pharmaceutically acceptable salt thereof.

11. The method of claim 10 wherein actaplanin factor H is administered to chickens.

12. The method of claim 10 wherein actaplanin factor H is administered to hogs.

* * * * *